US009271716B2

(12) United States Patent
Sengun

(10) Patent No.: US 9,271,716 B2
(45) Date of Patent: *Mar. 1, 2016

(54) SURGICAL CONSTRUCTS AND METHODS FOR SECURING TISSUE

(71) Applicant: Medos International Sàrl, Le Locle (CH)

(72) Inventor: Mehmet Ziya Sengun, Canton, MA (US)

(73) Assignee: MEDOS INTERNATIONAL SÀRL, Le Locle (CH)

(*) Notice: Subject to any disclaimer, the term of this patent is extended or adjusted under 35 U.S.C. 154(b) by 220 days.

This patent is subject to a terminal disclaimer.

(21) Appl. No.: 13/728,044

(22) Filed: Dec. 27, 2012

(65) Prior Publication Data

US 2014/0188163 A1  Jul. 3, 2014

(51) Int. Cl.
*A61B 17/06* (2006.01)
*A61B 17/04* (2006.01)

(52) U.S. Cl.
CPC ....... *A61B 17/0401* (2013.01); *A61B 17/06166* (2013.01); *A61B 2017/0403* (2013.01); *A61B 2017/0412* (2013.01); *A61B 2017/0458* (2013.01); *A61B 2017/0477* (2013.01); *A61B 2017/0496* (2013.01); *A61B 2017/06185* (2013.01)

(58) Field of Classification Search
CPC .............. A61B 17/0401; A61B 2017/0458; A61B 2017/0477; A61B 2017/0496; A61B 2017/06185; A61B 17/06166; A61B 2017/0403; A61B 2017/0412; A61B 2017/0473

USPC ......................................................... 606/232
See application file for complete search history.

(56) References Cited

U.S. PATENT DOCUMENTS

| 2,566,625 | A | 9/1951 | Nagelmann |
| 2,600,395 | A | 6/1952 | Domoj et al. |
| 2,697,624 | A | 12/1954 | Thomas et al. |

(Continued)

FOREIGN PATENT DOCUMENTS

| AU | 2008229746 A1 | 10/2008 |
| CA | 2772500 A1 | 9/2013 |

(Continued)

OTHER PUBLICATIONS

[No Author Listed] Arthroscopic Knot Tying Manual 2005. DePuy Mitek. 27 pages.

(Continued)

*Primary Examiner* — Ryan Severson
*Assistant Examiner* — Christian Knauss

(57) ABSTRACT

Suture constructs and methods are provided for securing soft tissue to bone. One exemplary embodiment of a construct includes a first limb, a second limb, a coaxial region, and a collapsible snare defined by the first and second limbs. The coaxial region can be formed by a portion of the second limb being disposed in a volume of the first limb, which allows for a low profile construct that is useful in various soft tissue repair procedures. The construct can be configured to be disposed in tissue to draw the tissue toward bone, and the coaxial region can be deconstructed so that the first and second limbs can be used to help secure the desired location of the tissue with respect to the bone. Various features of the construct and methods for using the same in a surgical procedure are also provided.

19 Claims, 3 Drawing Sheets

(56) References Cited

U.S. PATENT DOCUMENTS

| | | |
|---|---|---|
| 2,758,858 A | 8/1956 | Smith |
| 2,992,029 A | 7/1961 | Russell |
| 3,106,417 A | 10/1963 | Clow |
| 3,131,957 A | 5/1964 | Musto |
| 3,177,021 A | 4/1965 | Benham |
| 3,402,957 A | 9/1968 | Peterson |
| 3,521,918 A | 7/1970 | Hammond |
| 3,565,077 A | 2/1971 | Glick |
| 3,580,256 A | 5/1971 | Wilkinson et al. |
| 3,712,651 A | 1/1973 | Shockley |
| 3,752,516 A | 8/1973 | Mumma |
| 3,873,140 A | 3/1975 | Bloch |
| 4,029,346 A | 6/1977 | Browning |
| 4,036,101 A | 7/1977 | Burnett |
| 4,038,988 A | 8/1977 | Perisse |
| 4,105,034 A | 8/1978 | Shalaby et al. |
| 4,130,639 A | 12/1978 | Shalaby et al. |
| 4,140,678 A | 2/1979 | Shalaby et al. |
| 4,141,087 A | 2/1979 | Shalaby et al. |
| 4,186,921 A | 2/1980 | Fox |
| 4,205,399 A | 6/1980 | Shalaby et al. |
| 4,208,511 A | 6/1980 | Shalaby et al. |
| 4,319,428 A | 3/1982 | Fox |
| 4,403,797 A | 9/1983 | Ragland, Jr. |
| 4,510,934 A | 4/1985 | Batra |
| 4,572,554 A | 2/1986 | Janssen et al. |
| 4,792,336 A | 12/1988 | Hlavacek et al. |
| 4,870,957 A | 10/1989 | Goble et al. |
| 4,946,377 A * | 8/1990 | Kovach ............... 623/13.18 |
| 4,962,929 A | 10/1990 | Melton, Jr. |
| 4,987,665 A | 1/1991 | Dumican et al. |
| 5,062,344 A * | 11/1991 | Gerker ................ 87/8 |
| 5,098,137 A | 3/1992 | Wardall |
| 5,144,961 A | 9/1992 | Chen et al. |
| 5,156,616 A | 10/1992 | Meadows et al. |
| 5,178,629 A | 1/1993 | Kammerer |
| 5,217,495 A | 6/1993 | Kaplan et al. |
| 5,250,053 A | 10/1993 | Snyder |
| 5,250,054 A | 10/1993 | Li |
| 5,259,846 A | 11/1993 | Granger et al. |
| 5,263,984 A | 11/1993 | Li et al. |
| 5,279,311 A | 1/1994 | Snyder |
| 5,282,809 A | 2/1994 | Kammerer et al. |
| 5,284,485 A | 2/1994 | Kammerer et al. |
| 5,312,423 A | 5/1994 | Rosenbluth et al. |
| 5,318,575 A | 6/1994 | Chesterfield et al. |
| 5,376,118 A | 12/1994 | Kaplan et al. |
| 5,391,176 A | 2/1995 | de la Torre |
| 5,395,382 A | 3/1995 | DiGiovanni et al. |
| 5,405,352 A | 4/1995 | Weston |
| 5,450,860 A | 9/1995 | O'Connor |
| 5,454,820 A | 10/1995 | Kammerer et al. |
| 5,456,722 A | 10/1995 | McLeod et al. |
| 5,464,427 A | 11/1995 | Curtis et al. |
| 5,464,929 A | 11/1995 | Bezwada et al. |
| 5,472,446 A | 12/1995 | de la Torre |
| 5,527,323 A | 6/1996 | Jervis et al. |
| 5,534,011 A | 7/1996 | Greene, Jr. et al. |
| 5,540,703 A | 7/1996 | Barker, Jr. et al. |
| 5,549,618 A | 8/1996 | Fleenor et al. |
| 5,562,684 A | 10/1996 | Kammerer |
| 5,569,306 A | 10/1996 | Thal |
| 5,571,139 A | 11/1996 | Jenkins, Jr. |
| 5,573,286 A | 11/1996 | Rogozinski |
| 5,591,207 A | 1/1997 | Coleman |
| 5,593,189 A | 1/1997 | Little |
| 5,595,751 A | 1/1997 | Bezwada et al. |
| 5,597,579 A | 1/1997 | Bezwada et al. |
| 5,607,687 A | 3/1997 | Bezwada et al. |
| 5,618,552 A | 4/1997 | Bezwada et al. |
| 5,620,698 A | 4/1997 | Bezwada et al. |
| 5,628,756 A | 5/1997 | Barker |
| 5,645,850 A | 7/1997 | Bezwada et al. |
| 5,647,616 A | 7/1997 | Hamilton |
| 5,648,088 A | 7/1997 | Bezwada et al. |
| 5,667,528 A | 9/1997 | Colligan |
| 5,683,417 A | 11/1997 | Cooper |
| 5,683,419 A | 11/1997 | Thal |
| 5,685,037 A | 11/1997 | Fitzner et al. |
| 5,698,213 A | 12/1997 | Jamiolkowski et al. |
| 5,700,583 A | 12/1997 | Jamiolkowski et al. |
| 5,702,397 A | 12/1997 | Goble et al. |
| 5,709,708 A | 1/1998 | Thal |
| 5,716,368 A | 2/1998 | de la Torre et al. |
| 5,725,556 A | 3/1998 | Moser et al. |
| 5,728,109 A | 3/1998 | Schulze et al. |
| 5,741,332 A | 4/1998 | Schmitt |
| 5,749,898 A | 5/1998 | Schulze et al. |
| 5,782,864 A | 7/1998 | Lizardi |
| 5,814,069 A | 9/1998 | Schulze et al. |
| 5,859,150 A | 1/1999 | Jamiolkowski et al. |
| 5,899,920 A | 5/1999 | DeSatnick et al. |
| 5,941,900 A | 8/1999 | Bonutti |
| 5,964,783 A | 10/1999 | Grafton et al. |
| 5,971,447 A | 10/1999 | Steck, III |
| 6,024,758 A | 2/2000 | Thal |
| 6,045,574 A | 4/2000 | Thal |
| 6,143,017 A | 11/2000 | Thal |
| 6,221,084 B1 | 4/2001 | Fleenor |
| 6,267,766 B1 | 7/2001 | Burkhart |
| 6,296,659 B1 | 10/2001 | Foerster |
| 6,319,271 B1 | 11/2001 | Schwartz |
| 6,322,112 B1 | 11/2001 | Duncan |
| 6,517,578 B2 * | 2/2003 | Hein ............... 623/13.13 |
| 6,527,794 B1 | 3/2003 | McDevitt et al. |
| 6,527,795 B1 | 3/2003 | Lizardi |
| 6,540,750 B2 | 4/2003 | Burkhart |
| 6,547,807 B2 | 4/2003 | Chan et al. |
| 6,596,015 B1 | 7/2003 | Pitt et al. |
| 6,641,596 B1 | 11/2003 | Lizardi |
| 6,641,597 B2 | 11/2003 | Burkhart et al. |
| 6,652,563 B2 | 11/2003 | Dreyfuss |
| 6,660,023 B2 | 12/2003 | McDevitt et al. |
| 6,689,154 B2 | 2/2004 | Bartlett |
| 6,716,234 B2 | 4/2004 | Grafton et al. |
| 6,767,037 B2 | 7/2004 | Wenstrom, Jr. |
| 6,887,259 B2 | 5/2005 | Lizardi |
| 6,923,824 B2 | 8/2005 | Morgan et al. |
| 6,994,719 B2 | 2/2006 | Grafton |
| 7,029,490 B2 | 4/2006 | Grafton et al. |
| 7,048,754 B2 | 5/2006 | Martin et al. |
| 7,081,126 B2 | 7/2006 | McDevitt et al. |
| 7,217,279 B2 | 5/2007 | Reese |
| 7,226,469 B2 | 6/2007 | Benavitz et al. |
| 7,235,090 B2 | 6/2007 | Buckman et al. |
| 7,285,124 B2 | 10/2007 | Foerster |
| 7,309,337 B2 | 12/2007 | Colleran et al. |
| 7,338,502 B2 | 3/2008 | Rosenblatt |
| 7,381,213 B2 | 6/2008 | Lizardi |
| 7,390,332 B2 | 6/2008 | Selvitelli et al. |
| 7,455,684 B2 | 11/2008 | Gradel et al. |
| 7,582,105 B2 | 9/2009 | Kolster |
| 7,601,165 B2 | 10/2009 | Stone |
| 7,651,509 B2 | 1/2010 | Bojarski et al. |
| 7,654,321 B2 | 2/2010 | Zazovsky et al. |
| 7,658,750 B2 | 2/2010 | Li |
| 7,658,751 B2 | 2/2010 | Stone et al. |
| 7,682,374 B2 | 3/2010 | Foerster et al. |
| 7,695,495 B2 | 4/2010 | Dreyfuss |
| 7,703,372 B1 | 4/2010 | Shakespeare |
| 7,803,173 B2 | 9/2010 | Burkhart et al. |
| 7,875,043 B1 | 1/2011 | Ashby et al. |
| 7,883,528 B2 | 2/2011 | Grafton et al. |
| 7,883,529 B2 | 2/2011 | Sinnott et al. |
| 7,905,903 B2 | 3/2011 | Stone et al. |
| 7,905,904 B2 * | 3/2011 | Stone et al. ............... 606/232 |
| 7,959,650 B2 | 6/2011 | Kaiser et al. |
| 7,981,140 B2 | 7/2011 | Burkhart |
| 8,012,171 B2 | 9/2011 | Schmieding |
| 8,088,146 B2 | 1/2012 | Wert et al. |
| 8,114,128 B2 | 2/2012 | Cauldwell et al. |
| 8,118,836 B2 | 2/2012 | Denham et al. |
| 8,137,382 B2 | 3/2012 | Denham et al. |
| 8,231,653 B2 | 7/2012 | Dreyfuss |

(56) References Cited

U.S. PATENT DOCUMENTS

| | | |
|---|---|---|
| 8,231,654 B2 | 7/2012 | Kaiser et al. |
| 8,419,769 B2 | 4/2013 | Thal |
| 8,790,370 B2 | 7/2014 | Spenciner et al. |
| 8,814,905 B2 | 8/2014 | Sengun et al. |
| 8,821,543 B2 | 9/2014 | Hernandez et al. |
| 8,821,544 B2 | 9/2014 | Sengun et al. |
| 8,821,545 B2 | 9/2014 | Sengun |
| 8,894,684 B2 | 11/2014 | Sengun |
| 2002/0019649 A1 | 2/2002 | Sikora et al. |
| 2002/0029066 A1 | 3/2002 | Foerster |
| 2003/0004545 A1 | 1/2003 | Burkhart et al. |
| 2003/0050667 A1 | 3/2003 | Grafton et al. |
| 2003/0120309 A1 | 6/2003 | Colleran et al. |
| 2003/0130695 A1 | 7/2003 | McDevitt et al. |
| 2003/0229362 A1 | 12/2003 | Chan et al. |
| 2004/0093031 A1 | 5/2004 | Burkhart et al. |
| 2004/0098050 A1 | 5/2004 | Foerster et al. |
| 2004/0153074 A1 | 8/2004 | Bojarski et al. |
| 2004/0172062 A1 | 9/2004 | Burkhart |
| 2004/0236373 A1 | 11/2004 | Anspach |
| 2005/0033363 A1 | 2/2005 | Bojarski et al. |
| 2005/0119696 A1 | 6/2005 | Walters et al. |
| 2005/0137624 A1* | 6/2005 | Fallman .................. 606/213 |
| 2005/0187577 A1* | 8/2005 | Selvitelli et al. ........... 606/232 |
| 2005/0251208 A1 | 11/2005 | Elmer et al. |
| 2006/0106423 A1 | 5/2006 | Weisel et al. |
| 2006/0178680 A1 | 8/2006 | Nelson et al. |
| 2006/0178702 A1 | 8/2006 | Pierce et al. |
| 2006/0293710 A1 | 12/2006 | Foerster et al. |
| 2007/0027476 A1 | 2/2007 | Harris et al. |
| 2007/0032792 A1 | 2/2007 | Collin et al. |
| 2007/0060922 A1 | 3/2007 | Dreyfuss |
| 2007/0083236 A1* | 4/2007 | Sikora et al. ............... 606/232 |
| 2007/0135843 A1 | 6/2007 | Burkhart |
| 2007/0150003 A1 | 6/2007 | Dreyfuss et al. |
| 2007/0156148 A1 | 7/2007 | Fanton et al. |
| 2007/0156149 A1 | 7/2007 | Fanton et al. |
| 2007/0156150 A1 | 7/2007 | Fanton et al. |
| 2007/0156176 A1 | 7/2007 | Fanton et al. |
| 2007/0219557 A1* | 9/2007 | Bourque et al. ............ 606/72 |
| 2007/0219558 A1 | 9/2007 | Deutsch |
| 2007/0225719 A1 | 9/2007 | Stone et al. |
| 2007/0239209 A1* | 10/2007 | Fallman .................. 606/232 |
| 2008/0009901 A1 | 1/2008 | Redmond et al. |
| 2008/0009904 A1* | 1/2008 | Bourque et al. ............ 606/232 |
| 2008/0027446 A1* | 1/2008 | Stone et al. ............... 606/73 |
| 2008/0065114 A1 | 3/2008 | Stone et al. |
| 2008/0077182 A1 | 3/2008 | Geissler et al. |
| 2008/0091237 A1 | 4/2008 | Schwartz et al. |
| 2008/0103528 A1 | 5/2008 | Zirps et al. |
| 2008/0140092 A1 | 6/2008 | Stone et al. |
| 2008/0147063 A1 | 6/2008 | Cauldwell et al. |
| 2008/0188893 A1 | 8/2008 | Selvitelli et al. |
| 2008/0195205 A1 | 8/2008 | Schwartz |
| 2008/0208265 A1 | 8/2008 | Frazier et al. |
| 2008/0228265 A1 | 9/2008 | Spence et al. |
| 2008/0255613 A1* | 10/2008 | Kaiser et al. ............... 606/232 |
| 2008/0275469 A1 | 11/2008 | Fanton et al. |
| 2008/0312689 A1 | 12/2008 | Denham et al. |
| 2009/0023984 A1 | 1/2009 | Stokes et al. |
| 2009/0036905 A1 | 2/2009 | Schmieding |
| 2009/0054928 A1* | 2/2009 | Denham et al. ............ 606/232 |
| 2009/0062850 A1 | 3/2009 | Ken |
| 2009/0062854 A1* | 3/2009 | Kaiser et al. ............... 606/232 |
| 2009/0082805 A1* | 3/2009 | Kaiser et al. ............... 606/228 |
| 2009/0082807 A1 | 3/2009 | Miller et al. |
| 2009/0088798 A1 | 4/2009 | Snyder et al. |
| 2009/0099598 A1 | 4/2009 | McDevitt et al. |
| 2009/0138042 A1 | 5/2009 | Thal |
| 2009/0281568 A1 | 11/2009 | Cendan et al. |
| 2009/0281581 A1 | 11/2009 | Berg |
| 2009/0287246 A1 | 11/2009 | Cauldwell et al. |
| 2009/0306711 A1* | 12/2009 | Stone et al. ............... 606/232 |
| 2009/0312776 A1* | 12/2009 | Kaiser et al. ............... 606/148 |
| 2009/0312794 A1 | 12/2009 | Nason et al. |
| 2009/0318958 A1 | 12/2009 | Ochiai |
| 2010/0004683 A1 | 1/2010 | Hoof et al. |
| 2010/0016892 A1* | 1/2010 | Kaiser et al. ............... 606/232 |
| 2010/0094425 A1 | 4/2010 | Bentley et al. |
| 2010/0162882 A1* | 7/2010 | Shakespeare .............. 87/6 |
| 2010/0204730 A1 | 8/2010 | Maiorino et al. |
| 2010/0249809 A1 | 9/2010 | Singhatat et al. |
| 2010/0249834 A1 | 9/2010 | Dreyfuss |
| 2010/0256677 A1 | 10/2010 | Albertorio et al. |
| 2010/0292732 A1 | 11/2010 | Hirotsuka et al. |
| 2010/0292792 A1* | 11/2010 | Stone et al. ............... 623/13.14 |
| 2011/0022083 A1* | 1/2011 | DiMatteo et al. ........... 606/228 |
| 2011/0077667 A1 | 3/2011 | Singhatat et al. |
| 2011/0190815 A1 | 8/2011 | Saliman |
| 2011/0208240 A1 | 8/2011 | Stone et al. |
| 2011/0213416 A1* | 9/2011 | Kaiser .................. 606/232 |
| 2011/0238111 A1 | 9/2011 | Frank |
| 2011/0270278 A1 | 11/2011 | Overes et al. |
| 2012/0046693 A1* | 2/2012 | Denham et al. ............ 606/232 |
| 2012/0053630 A1 | 3/2012 | Denham et al. |
| 2012/0059417 A1 | 3/2012 | Norton et al. |
| 2012/0101523 A1 | 4/2012 | Wert et al. |
| 2012/0130423 A1 | 5/2012 | Sengun et al. |
| 2012/0130424 A1 | 5/2012 | Sengun et al. |
| 2012/0150223 A1 | 6/2012 | Manos et al. |
| 2012/0165864 A1 | 6/2012 | Hernandez et al. |
| 2012/0179199 A1 | 7/2012 | Hernandez et al. |
| 2012/0253389 A1 | 10/2012 | Sengun et al. |
| 2012/0253390 A1 | 10/2012 | Sengun |
| 2012/0296375 A1 | 11/2012 | Thal |
| 2013/0110165 A1 | 5/2013 | Burkhart et al. |
| 2013/0158598 A1 | 6/2013 | Lizardi |
| 2013/0261664 A1 | 10/2013 | Spenciner et al. |
| 2013/0296895 A1 | 11/2013 | Sengun |
| 2013/0296896 A1 | 11/2013 | Sengun |
| 2013/0296931 A1 | 11/2013 | Sengun |
| 2013/0296934 A1 | 11/2013 | Sengun |
| 2014/0081324 A1 | 3/2014 | Sengun |
| 2014/0188164 A1 | 7/2014 | Sengun |
| 2014/0277132 A1 | 9/2014 | Sengun et al. |
| 2014/0330312 A1 | 11/2014 | Spenciner et al. |
| 2014/0343606 A1 | 11/2014 | Hernandez et al. |
| 2014/0343607 A1 | 11/2014 | Sengun et al. |
| 2015/0012038 A1 | 1/2015 | Sengun et al. |

FOREIGN PATENT DOCUMENTS

| | | |
|---|---|---|
| EP | 0870471 A1 | 10/1998 |
| EP | 1 199 035 A1 | 4/2002 |
| EP | 1 707 127 A1 | 10/2006 |
| EP | 2 277 457 A1 | 1/2011 |
| EP | 2 455 003 A2 | 5/2012 |
| EP | 2 572 650 A1 | 3/2013 |
| WO | 95/19139 A1 | 7/1995 |
| WO | 97/17901 A1 | 5/1997 |
| WO | 98/11825 A1 | 3/1998 |
| WO | 01/06933 A2 | 2/2001 |
| WO | 03/022161 A1 | 3/2003 |
| WO | 2007/109769 A1 | 9/2007 |

OTHER PUBLICATIONS

[No Author Listed] Gryphon Brochure. DePuy Mitek. 2 pages (undated).

Allcock, The Encyclopedia of Polymer Science, vol. 13, pp. 31-41, Wiley Intersciences, John Wiley & Sons, 1988.

Cohn et al., Biodegradable PEO/PLA block copolymers. J Biomed Mater Res. Nov. 1988;22(11):993-1009.

Cohn et al., Polym Preprint. 1989;30(1):498.

Dahl et al., Biomechanical characteristics of 9 arthroscopic knots. Arthroscopy. Jun. 2010;26(6):813-8.

EP Search Report for Application No. 11190157.5 issued Feb. 27, 2012. (8 pages).

EP Search Report for Application No. 11190159.1 issued Feb. 21, 2012. (8 pages).

(56) References Cited

OTHER PUBLICATIONS

Extented European Search Report for Application No. 11195100.0 issued Oct. 17, 2012. (7 pages).

Extended European Search Report for Application No. 11190157.5 issued Jul. 6, 2012. (10 pages).

Extended European Search Report for Application No. 11190159.1 issued Jul. 6, 2012. (11 pages).

Heller, Handbook of Biodegradable Polymers, edited by Domb, et al., Hardwood Academic Press, pp. 99-118 (1997).

International Search Report for Application No. PCT/US2011/067119, mailed Jun. 4, 2012. (6 pages).

Kemnitzer et al., Handbook of biodegradable Polymers. Eds. Domb et al. Hardwood Acad. Press. 1997;251-72.

Vandorpe et al., Handbook of Biodegradable Polymers, edited by Domb, et al., Hardwood Acad. Press, pp. 161-182 (1997).

[No Author Listed] Versalok Anchor. Brochure. DePuy Mitek, a Johnson & Johnson company, 92 pages, 2007.

Extended European Search Report for Application No. 13166905.3 issued Aug. 13, 2013 (9 Pages).

Extended European Search Report for Application No. 13166907.9, issued Aug. 1, 2013 (6 pages).

Extended European Search Report for Application No. 13166908.7, issued Aug. 23, 2013 (8 pages).

Extended European Search Report for Application No. 13199724.9 issued Apr. 4, 2014 (6 Pages).

Extended European Search Report for Application No. 13185425.9 issued Dec. 16, 2013 (9 Pages).

\* cited by examiner

SURGICAL CONSTRUCTS AND METHODS FOR SECURING TISSUE

FIELD

The present disclosure relates to surgical constructs and methods for securing soft tissue to bone, and more particularly relates to surgical constructs having reduced profiles for use in securing soft tissue while minimizing or eliminating the tying of knots to tension and secure the tissue.

BACKGROUND

A common injury, especially among athletes and people of advancing age, is the complete or partial detachment of tendons, ligaments, or other soft tissues from bone. Tissue detachment may occur during a fall, by overexertion, or for a variety of other reasons. Surgical intervention is often needed, particularly when tissue is completely detached from its associated bone. Currently available devices for tissue attachment include screws, staples, suture anchors, and tacks. Currently available devices for patients of advancing age can be particularly insufficient due to soft and weak bones leading to inadequate fixation between the anchor and bones and the anchors and filaments with which the anchors are coupled.

Repair constructs made from one or more surgical filaments are typically used in soft tissue repair procedures to secure the tissue in a desired location. The repair constructs are typically disposed through one or more portions of the tissue to be repaired, which can cause trauma to the tissue, and are often coupled to anchors disposed in bone to which the tissue is to be approximated. While devices and techniques have been developed to help minimize trauma associated with passing repair constructs through tissue, there is still room for further improvement. For example, some repair constructs typically include a sleeve disposed around at least a portion of the limbs of filament of the construct. The sleeve can assist in minimizing trauma to tissue, and also in managing the limbs of suture while the construct is being disposed through tissue. However, the sleeve still adds extra size and cost to the construct. Additionally, there remains a desire to minimize the number of knots used in conjunction with the repair construct when performing soft tissue repair procedures. A variety of different knots, such as sliding knots, can be used to help draw and secure soft tissue with respect to bone. Although the tying of knots at a surgical site is common, in some instances knots can have a tendency to slip, which in turn can cause a loss of tension between the tissue and bone. This drawback is sometimes referred to as a loss of "loop security." In addition to this "loop security" issue, conventional knots typically have an overall size that can be obstructive or intrusive, especially in tight joints, which may damage cartilage or other tissue by abrasion with the knot.

It is therefore desirable to provide repair constructs and methods that reduce the amount of trauma associated with using repair constructs while maintaining or improving the holding strength such constructs and methods can provide. It is also desirable to provide constructs and methods for use in soft tissue repair that minimize or eliminate the number and size of knots to be tied by a surgeon, particularly during arthroscopic repair procedures.

SUMMARY

Surgical constructs and methods are generally provided for securing soft tissue to bone. In one exemplary embodiment the surgical construct includes a first limb, a second limb that is shorter than the first limb, a coaxial region, and a collapsible snare defined by the first limb and the second limb. The coaxial region can be formed by a terminal end of the second limb being disposed within a volume of the first limb, with the snare being located on one side of the coaxial region and a terminal end of the first limb being disposed on the other side of the coaxial region. The first and second limbs can be from the same surgical filament. In other embodiments the first and second limbs can be from separate surgical filaments. The surgical filament(s) can include, for example, braided suture. The collapsible snare can include a slidable knot that adjusts a size of an opening defined by the snare by moving towards and away from the coaxial region. In one embodiment, the size of the opening defined by the snare decreases when the slidable knot moves away from the coaxial region and increases when the slidable knot moves towards the coaxial region.

The first limb of the construct can be cannulated at the coaxial region. A length of the coaxial region can be substantially shorter than a length of the first limb extending from the other side of the coaxial region. The length of the coaxial region can also be substantially shorter than lengths of the first and second limbs on the side of the coaxial region on which the snare is located. The coaxial region can be configured to be deconstructed after placement of the suture construct at a surgical location. This can allow the first and second limbs to be used to secure a location of the suture construct, for instance after tissue coupled to the suture construct has been advanced to a desirable location proximate to bone.

The suture construct can also include a suture anchor having a filament engagement feature. A portion of the construct can be slidably disposed around a portion of the filament engagement feature. In some embodiments the snare can extend from one side of the anchor and the coaxial region can extend from another side of the anchor. In some other embodiments the portion of the first limb that is disposed on the other side of the coaxial region can engage the filament engagement feature of the anchor such that this portion of the first limb extends from both sides of the anchor.

One exemplary embodiment of a surgical repair method includes selecting a surgical repair construct having a snare defined by a first filament limb and a second filament limb, and a coaxial region formed by a terminal end of the second filament limb being disposed within a volume of the first filament limb. The method can further include fixing an anchor in bone in proximity to detached soft tissue. Further, a terminal end of the first filament limb can be passed through a portion of the detached soft tissue and around an engagement feature of the anchor. The resulting configuration can be one in which the snare extends from one side of the anchor and the terminal end of the first filament limb extends from another side of the anchor. Still further, the method can include passing the terminal end of the first filament limb through the snare, collapsing the snare to engage the soft tissue, advancing the collapsed snare distally to bring the tissue into proximity with the bone, and removing the terminal end of the second filament limb from the volume of the first filament limb to eliminate the coaxial region. The first and second filament limbs can then be used to tie one or more knots proximate to the collapsed snare to maintain the tissue at a desired location in proximity to the bone. The passing, collapsing, and advancing steps, however, can be effected without tying a knot in the first or second filament limbs.

In some embodiments at least one of a first end of the surgical repair construct and a second end of a surgical repair construct can be passed through a surgical cannula. Further, in some embodiments the method can include passing the terminal end of the first filament limb through a second portion of the detached soft tissue. The step of collapsing the snare can include collapsing the snare around the first filament limb extending from the coaxial region and disposed on an opposite side of the coaxial region from the snare. Alternatively, in some embodiments the step of passing the terminal end of the first filament limb through the snare can include passing the coaxial region through the snare and then collapsing the snare can include collapsing the snare around the first filament limb and the second filament limb disposed therethrough.

The anchor that is fixed in bone can include a suture shuttle filament slidably coupled to the engagement feature. The suture shuttle filament can have a free end and a receiving end and can be coupled to the anchor prior to the step of passing a terminal end of the first filament limb through a portion of the detached soft tissue. In such embodiments, the step of passing a terminal end of the first filament limb through a portion of the detached soft tissue and around an engagement feature of the anchor can rely on the suture shuttle filament to assist in moving the surgical repair construct. More particularly, the terminal end of the first filament can be coupled to the receiving end of the suture shuttle filament and a force can be applied to the free end of the suture shuttle filament to move the receiving end of the suture shuttle filament, and thus the terminal end of the first filament limb, toward and then around the engagement feature of the anchor. The suture shuttle filament can then pass around and out of contact with the engagement feature of the anchor, thereby allowing the surgical repair construct to be in direct contact with the engagement feature. Eventually, the resulting configuration is the same as described above, with the snare extending from one side of the anchor and the coaxial region extending from another side of the anchor. In some embodiments the suture shuttle filament can be disposed through the detached soft tissue in two locations. As a result, the surgical repair construct can also be disposed through the detached soft tissue in two locations following the step of applying a force to the free end of the suture shuttle filament.

BRIEF DESCRIPTION OF DRAWINGS

This invention will be more fully understood from the following detailed description taken in conjunction with the accompanying drawings, in which.

DETAILED DESCRIPTION

Figure 1A:
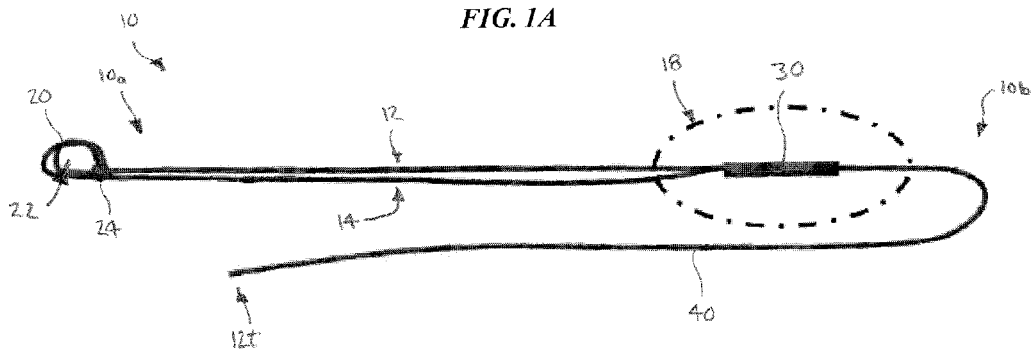
FIG. 1A is a schematic view of one exemplary embodiment of a surgical repair construct.

Certain exemplary embodiments will now be described to provide an overall understanding of the principles of the structure, function, manufacture, and use of the constructs and methods disclosed herein. One or more examples of these embodiments are illustrated in the accompanying drawings.

Those skilled in the art will understand that the constructs and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Additionally, to the extent that linear or circular dimensions are used in the description of the disclosed constructs and methods, such dimensions are not intended to limit the types of shapes that can be used in conjunction with such constructs and methods. A person skilled in the art will recognize that an equivalent to such linear and circular dimensions can easily be determined for any geometric shape. Sizes and shapes of the constructs, and the components thereof, can depend at least on the anatomy of the subject in which the constructs will be used, the size and shape of components with which the constructs will be used, and the methods and procedures in which the constructs will be used.

The figures provided herein are not necessarily to scale. Further, to the extent arrows are used to describe a direction a component can be tensioned or pulled, these arrows are illustrative and in no way limit the direction the respective component can be tensioned or pulled. A person skilled in the art will recognize other ways and directions for creating the desired tension or movement. Likewise, while in some embodiments movement of one component is described with respect to another, a person skilled in the art will recognize that other movements are possible. By way of non-limiting example, in embodiments in which a sliding knot is used to help define a snare, a person skilled in the art will recognize that different knot configurations can change whether moving the knot in one direction will cause a size of an opening defined by the snare will increase or decrease. Additionally, a number of terms may be used throughout the disclosure interchangeably but will be understood by a person skilled in the art. By way of non-limiting example, the terms "suture" and "filament" may be used interchangeably.

Surgical repair constructs and methods for soft tissue repair are generally provided and they generally involve the use of surgical filaments that are configured in a variety of manners to minimize and/or eliminate the tying of knots during a surgical procedure. The constructs described herein provide superior strength for use in a number of different surgical procedures, such as rotator cuff and instability repair procedures and other types of tendon and tissue repair procedures. The designs of the constructs described herein are such that they have a particularly low profile, thereby allowing a construct to pass through the tissue with minimal trauma to the tissue and to become associated with the tissue without tying knots. The low profile results from inserting one limb of filament into another and eliminating any sort of sleeve, which is often used to assist in shuttling limbs of filament through tissue. Further, the designs of the constructs are such that they limit the number of filaments that are used to feed the construct through the tissue, or otherwise associate the construct with tissue. As described, a single limb of filament can be used to associate the construct with tissue that is being attached to bone, thereby assisting a surgeon with suture management.

As shown by one exemplary embodiment of a surgical repair construct 10 in FIG. 1A, the constructs of the present disclosure are generally formed from a single elongate filament that is folded to form a first limb 12 and a second limb 14. The first limb 12 can generally be longer than the second limb 14, and the two limbs can be used to form both a snare 20 and a coaxial region 30 as described in greater detail below. The snare 20, which is disposed on a first end 10a of the construct 10, can be configured to receive an opposite end 10b of the construct 10 and is operable to collapse around a portion of the construct disposed in an opening 22 thereof. The coaxial region 30 is generally configured to allow the shorter second limb 14 to be disposed within a volume of the first limb 12, thereby eliminating any additional component for suture management, such as a sleeve. The first limb 12 can then extend beyond the coaxial region 30 to form a tail 40 of the construct 10. The tail 40 can assist a surgeon with inserting the construct 10 to a desired location for a surgical procedure.

The collapsible snare 20 can be formed using any number of techniques known to those skilled in the art. In the illustrated embodiment the first and second limbs 12, 14 are formed to include a sliding knot 24. The sliding knot 24 is configured such that as it moves toward the coaxial region 30, a size of the opening 22 defined by the snare 20 increases, and as the knot 24 moves away from the coaxial region 30, the size of the opening 22 decreases. Some exemplary knot types include a Buntline Hitch, a Tennessee Slider, a Duncan Loop, and a Hangman's Noose. A person skilled in the art will understand that in other configurations, a size of the opening defined by the snare may be adjusted in different manners, depending on the type of knot, desired use, etc. Some exemplary snare and formations thereof are described in U.S. Published Patent Application No. 2012/0130424 of Sengun et al. and U.S. application Ser. No. 13/465,288, entitled "Systems, Devices, and Methods for Securing Tissue, and filed May 7, 2012, the content of which is incorporated by reference in their entireties.

Further, in some embodiments a snare-retaining member (not shown) can be disposed across the first and second limbs 12, 14, between the snare 20 and the coaxial region 30, for instance to prevent the unintentional collapse of the opening 22 of the snare 20, such as while the construct 10 is being moved through tissue. A snare-retaining member can include a flexible member or pin, such as the flexible members and pins described in U.S. application Ser. No. 13/465,299, entitled "Systems, Devices, and Methods for Securing Tissue" and filed May 7, 2012, the content of which is incorporated by reference in its entirety.

Figure 1B:
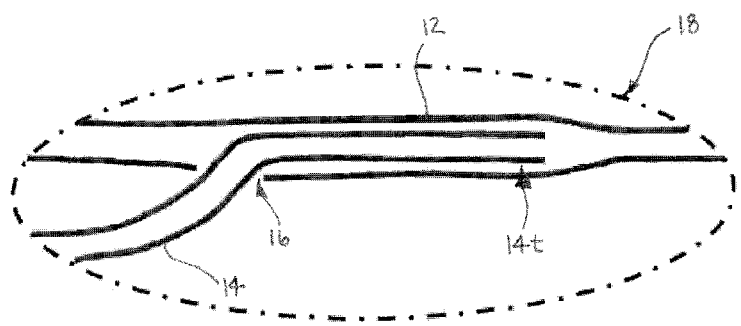
FIG. 1B is a detail view of a coaxial region of the surgical repair construct of FIG. 1A.

The coaxial region 30 in the illustrated embodiment is formed by passing terminal end 14t of the second limb 14 into a volume of the first limb 12. As shown in FIG. 1B, at least a portion of the first limb 12 can be cannulated, and an opening 16 on a side of the first limb 12 allows the second limb 14 to be disposed in the first limb 12. The opening 16 can be created manually by forming a hole in the side of the first limb 12 and removing a core of the first limb 12 so that there is space to receive the second limb 14. Alternatively, the filament of the first limb 12 can be a braided suture with a core removed from at least the portion of the first limb 12 that is part of the coaxial region 30, thereby allowing the first limb 12 to receive the second limb 14. In other embodiments a core of a filament, braided or otherwise, is not removed and the second limb 14 is still disposed in first limb 12 using techniques known to those skilled in the art. The junction 18 at which the second limb 14 engages the first limb 12 can be a self-maintaining junction. As a result, pulling on the tail 40 of the surgical construct 10 does not cause the second limb 14 to pull out of the first limb 12. Rather, pulling on the tail 40 can actually force the first limb 12 to collapse around the second limb 14, thereby providing sufficient friction between the two limbs 12 and 14 to hold them together. The two limbs 12 and 14, however, can be separated manually at the junction 18 by applying a sufficient amount of force. Although in the illustrated embodiment the junction 18 is formed by inserting the terminal end 14t of the second limb 14 into a portion of the first limb 12, a person skilled in the art will understand other ways by which the junction can be formed without departing from the spirit of the present disclosure.

The tail 40 of the construct 10 is formed by the remaining portion of the first limb 12 that extends beyond the coaxial region 30. The tail 40 can be used to help lead insertion of the construct 10 in tissue, coupling the construct 10 to a suture anchor, and leading the second end 10b of the construct 10 into the opening 22 of the snare 20 during tissue repair procedures, among other things. Accordingly, a length and thickness of the tail 40 can be such that it ensures robust shuttling of the construct 10 during a surgical procedure.

The filament used to form the first and second limbs 12 and 14 can be any type and material typically used as filaments, including a cannulated filament, a braided filament, and a mono filament. The type and strength of the filament can depend, at least in part, on the other materials of the construct, if any, such as an anchor, the tissue and other components through which it will be passed or coupled to, and the type of procedure in which it is used. In one exemplary embodiment the filament is a #0 filament (about 26 gauge to about 27 gauge), such as an Orthocord™ filament that is commercially available from DePuy Mitek, Inc., DePuy Mitek Inc., 325 Paramount Drive, Raynham, Mass. 02767, or an Ethibond™ filament that is commercially available from Ethicon, Inc., Route 22 West, Somerville, N.J. 08876. A portion of the core of the filament can be removed to form a cannulated portion of the first limb 12 for use in the coaxial region 30. The thickness of the filament should provide strength in the connection but at the same time minimize the trauma caused to tissue through which it passes. In some embodiments the filament can have a size between about a #5 filament (about 20 gauge to about 21 gauge) and about a #3-0 filament (about 29 gauge to about 32 gauge). Orthocord™ suture is approximately fifty-five to sixty-five percent PDS™ polydioxanone, which is bioabsorbable, and the remaining thirty-five to forty-five percent ultra high molecular weight polyethylene, while Ethibond™ suture is primarily high strength polyester. The amount and type of bioabsorbable material, if any, utilized in the filaments of the present disclosure is primarily a matter of surgeon preference for the particular surgical procedure to be performed. Additionally, although in the illustrated embodiment a single filament is used to form the first and second limbs 12 and 14, a separate filament can be used for each of the first and second limbs 12 and 14 without departing from the spirit of the disclosures provided herein.

Figure 1C:
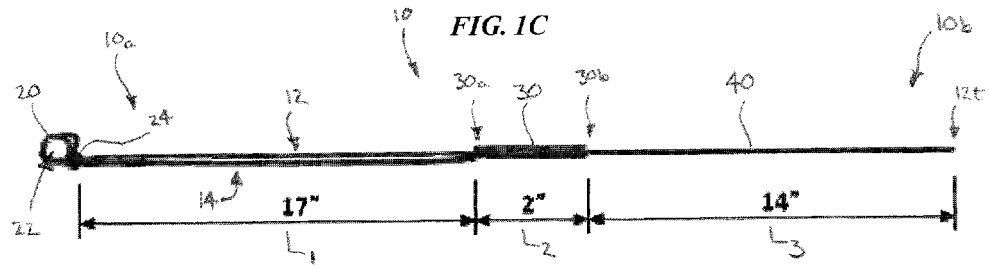
FIG. 1C is a schematic view of the surgical repair construct of FIG. 1A illustrating one non-limiting example of potential lengths of portions of the construct.

The lengths of the various portions of the construct 10 can likewise depend, at least in part, on the other materials of the construct, if any, the tissue and other components through which it will be passed or coupled to, the lengths of the various portions of the construct, and the type of procedure in which the construct is used. The various portions include the portions of the first and second limbs 12 and 14 on the side of the coaxial region 30 the snare 20 is located, the coaxial region 30, and the tail 40. In the illustrated embodiment the coaxial region 30 is substantially shorter than both the tail 40 and the portions of the first and second limbs 12 and 14 on the side of the coaxial region 30 the snare 20 is located. FIG. 1C provides one schematic representation of a possible proportional length scheme comparing a length $L_1$ of a region between the knot 24 and one end 30a of the coaxial region 30, a length $L_2$ of the coaxial region 30, and a length $L_3$ from the other end 30b of the coaxial region 30 to a terminal end 12t of the first limb 12. As shown the length $L_1$ can be about 17 inches, the length $L_2$ can be about 2 inches, and the length $L_3$ can be about 14 inches. A person skilled in the art will recognize that these lengths can change during the course of a procedure. For example, as the sliding knot 24 is selectively moved toward or away from the coaxial region 30, the length $L_1$ will change. Likewise, a surgeon may be able to manually adjust the lengths $L_2$ and $L_3$. Further, the lengths provided in the illustrated embodiment of FIG. 1C in no way limit values of the lengths $L_1$, $L_2$, and $L_3$. Generally, the length $L_1$ can be approximately in the range of about 5 inches to about 30 inches, the length $L_2$ can be approximately in the range of about 0.5 inches to about 8 inches, and the length $L_3$ can be approximately in the range of about 6 inches to about 40 inches.

Figure 2:
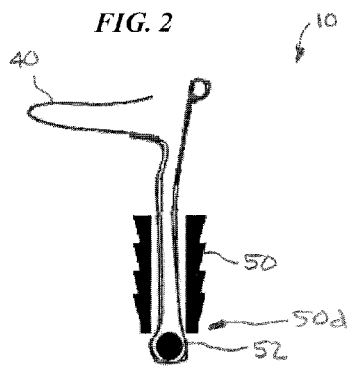
FIG. 2 is a schematic view of the surgical repair construct of FIG. 1A coupled to a suture anchor.

As shown in FIG. 2, the construct 10 can be coupled to a suture anchor 50. The suture anchor 50 can include one or more filament engagement features, such as the filament engagement feature 52 disposed at a distal end 50d of the anchor 50. In the illustrated embodiment, the snare 20 extends from one side of the anchor and the coaxial region 30 extends from the other side of the anchor. However, in other embodiments the tail 40 can be engaged with the filament engagement feature 52 of the anchor 50 such that the tail 40 extends from both sides of the anchor, for instance as illustrated in FIG. 4D and described further below. Such a configuration can allow the portion of the first and second limbs 12 and 14 extending between the knot 24 and the coaxial region 30 to not be within joint space, thereby assisting with suture management by minimizing the number of limbs emanating from the anchor 50.

As described in greater detail below, in some embodiments the construct 10 can be pre-loaded on the suture anchor 50 prior to insertion of the anchor 50 to a surgical location, while in other embodiments the construct 10 is loaded onto the suture anchor 50 after the anchor is positioned at the surgical location. One skilled in the art will appreciate that a variety of suture anchor types can be used in conjunction with the constructs provided herein. For example, in some embodiments the anchor can be a Gryphon™ anchor that is commercially available from DePuy Mitek, Inc. The constructs described herein can be single-loaded or double-loaded onto a Gryphon™ anchor.

As a result of the configurations of the construct 10 described herein, anchors used in conjunction with the construct 10 can be smaller than previous anchors used in tissue repairs at least because a smaller diameter or thickness of construct can be associated with the anchor. Further, Gryphon™ anchors are merely non-limiting examples of anchor types that can be used in conjunction with the disclosures provided herein. Other types of hard and soft anchors can also be used. Some examples of such anchors include a Healix Ti™ anchor, which is commercial available from DePuy Mitek, Inc., as well as anchors described in U.S. application Ser. No. 13/465,376, entitled "Systems, Devices, and Methods for Securing Tissue Using Snare Assemblies and Soft Anchors," filed May 7, 2012, and U.S. application Ser. No. 13/623,429, entitled "Systems, Devices, and Methods for Securing Tissue Using Hard Anchors," filed Sep. 20, 2012, the content of which is incorporated by reference in their entireties.

Figure 3:
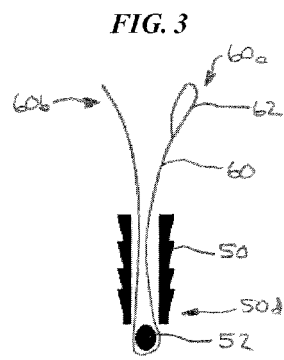
FIG. 3 is schematic view of a suture shuttle filament coupled to the suture anchor of FIG. 2.

FIG. 3 illustrates one exemplary embodiment of a suture shuttle filament 60 coupled to the suture anchor 50. Again, virtually any type of suture anchor can be used in conjunction with the shuttles and constructs provided herein, but the illustrated anchor 50 is a Healix™ anchor. The shuttle 60 can be slidably engaged with the anchor 50 at the filament engagement feature 52 such that a first end 60a of the shuttle 60 extends from one side of the anchor 50 and a second end 60b of the shuttle 60 extends from the other side of the anchor 50. The first end 60a can be configured to be coupled to a repair construct, such as the repair construct 10 of FIG. 1A. As shown, the first end 60a includes a fixed loop 62, but any other suitable coupling mechanism can be used at the first end 60a without departing from the spirit of the present disclosure. For example, the first end 60a can include a clip or a like element to clamp around a repair construct. In other embodiments the loop 62 can be a collapsible snare. Once the repair construct 10 is coupled to the first end 60a, the second end 60b can be used to position the repair construct 10 in a desired location as described below with respect to FIGS. 4A-4D.

One exemplary embodiment of a method for performing a rotator cuff repair using the repair construct 10 of FIG. 1A in conjunction with the suture shuttle filament 60 of FIG. 3 is illustrated in FIGS. 4A-4I. A surgical opening can be formed through skin 100 and a cannula can be passed therethrough to create a surgical repair site in a manner well known to those skilled in the art. Although cannulas are often used to define a channel through which the procedure can be performed, the cannula is not shown in FIGS. 4A-4I for ease of illustration. Accordingly, to the extent the figures show components of the construct passing through skin 100, these components would typically be extending through the cannula, which itself is passed through the skin 100. Further, although the constructs and methods described herein are particularly useful for minimally invasive surgery, such as arthroscopic surgery, they can also be used in open surgical procedures.

Figure 4A:
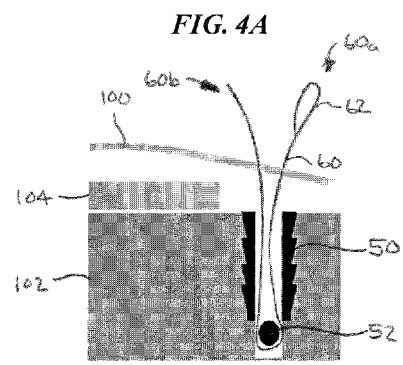
FIGS. 4A-4I are sequential view of one exemplary embodiment for using the surgical repair construct of FIG. 1A to secure tissue to bone.

As shown in FIG. 4A, the anchor 50 and suture shuttle filament 60 illustrated in FIG. 3 can be fixated into bone 102 using ordinary techniques, such as by using a driver to screw or tap the anchor 50 into place. In the illustrated embodiment the suture shuttle filament 60, which includes the first end 60a having the loop 62 formed therein, is already coupled thereto, although in other embodiments the suture shuttle filament 60 can be slidingly coupled to the anchor 50 after the anchor 50 is positioned at its desired location.

Figure 4B:
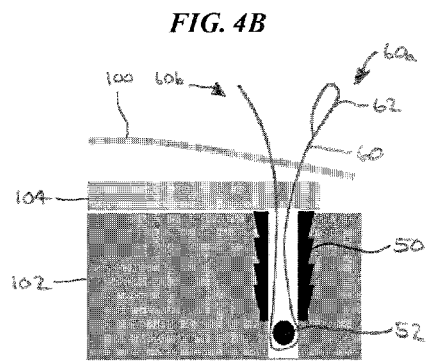
Figure 4C:
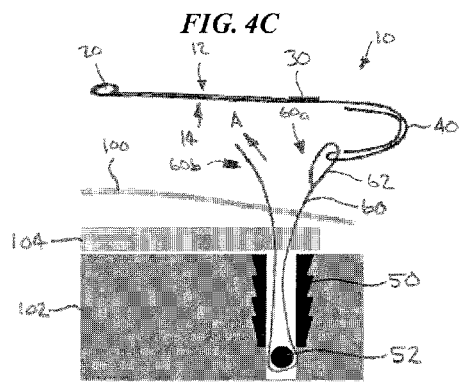
Figure 4D:
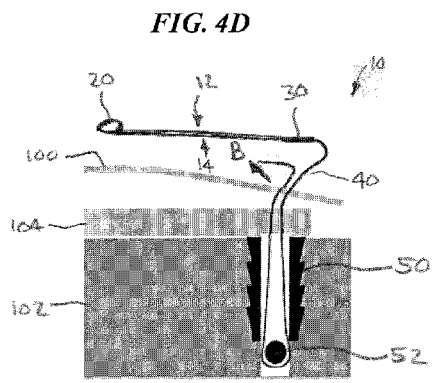
Figure 4E:
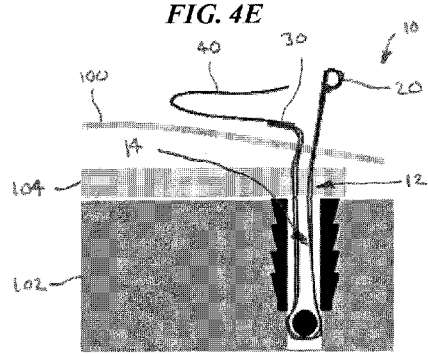

As shown in FIG. 4B, the first and second ends 60a, 60b of the suture shuttle filament 60 can be passed through detached soft tissue, such as tendon 104. As shown in FIG. 4C, a portion of the tail 40 of the repair construct 10 of FIG. 1A can be passed through the loop 62, thereby, at least temporarily, coupling the repair construct 10 to the shuttle 60. A force approximately in the direction A can then be applied to the second end 60b to pull the first end 60a, and thus the repair construct 10, through the tendon 104 at a first location, around the filament engagement feature 52, and through the tendon 104 at a second location. As a result, as shown in FIG. 4D, the tail 40 can be disposed around the filament engagement feature 52 and, depending on the length of the tail 40, can extend on both sides of the anchor 50. Once the suture shuttle filament 60 has moved the construct 10 to a location that allows a surgeon to grasp the tail 40, either manually or by the use of a surgical tool, the suture shuttle filament 60 can be decoupled from the repair construct 10. The tail 40 can then be used to continue to shuttle the construct 10 to a desired location, for instance by applying a force in a direction B. Alternatively, the shuttle 60 can continue to be used to shuttle the construct 10 to a desired location for the construct 10 before the shuttle 60 is de-coupled from the construct 10. One non-limiting, exemplary location for the construct 10 is shown in FIG. 4E, in which the snare 20 is disposed on one side of the anchor 50 and the coaxial region 30 is disposed on the other side of the anchor 50, with portions of the first and second limbs 12, 14 that are disposed between the snare 20 and the coaxial region 30 in sliding engagement with the filament engagement feature 52.

Figure 4F:
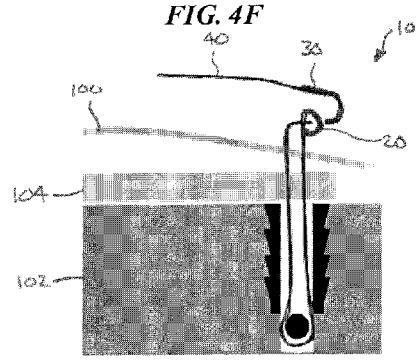

As shown in FIG. 4F, the tail 40 and the coaxial region 30 can be passed through the snare 20 such that portions of the first and second limbs 12, 14 that are disposed between the snare 20 and the coaxial region 30 are disposed within the opening 22 of the snare 20, thereby allowing the tendon 104 through which the construct 10 is disposed to be captured. The snare 20 can then be collapsed or dressed around the portions of the first and second limbs 12, 14 disposed therethrough, with the snare 20 remaining distal of the coaxial region 30. In embodiments in which a snare-retaining member is disposed through a portion of the construct 10 to prevent the intentional collapse of the snare 20, the snare-retaining member can be removed prior to collapsing the snare 20.

Alternatively, in other embodiments just the tail 40 can be passed through the snare such that only a portion of the first limb 12 is disposed within the opening 22 of the snare 20, thereby allowing the tendon 104 through which the construct 10 is disposed to be captured. The snare 20 can then be collapsed or dressed around the portion of the tail 40 disposed therethrough. Although in such an embodiment the coaxial region 30 is distal of the snare 20, the snare 20 can be subsequently slid distally toward the tendon to allow the coaxial region 30 to become proximal of the snare 20, as described below with respect to FIG. 4G.

Figure 4G:
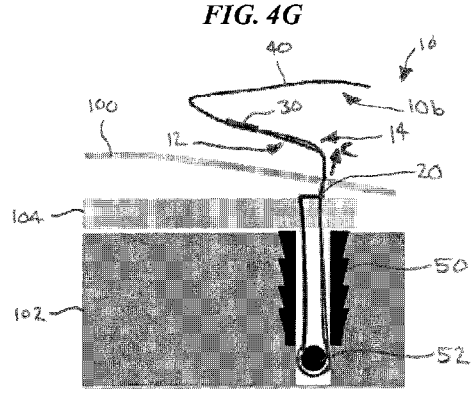

As shown in FIG. 4G, tension can be applied to the second end 10b of the construct 10 by pulling approximately in a direction C, thereby causing the collapsed snare 20 to slide distally toward the tendon 104 in a zip-line like manner until the snare 20 is adjacent to the tendon 104. Alternatively, tension can be applied to the second end 10b before the snare 20 is dressed and after the snare 20 is adjacent to the tendon 104, or some combination of the two actions can be used, such as partially dressing the snare 20 before zip-lining it toward the tendon 104.

Figure 4H:
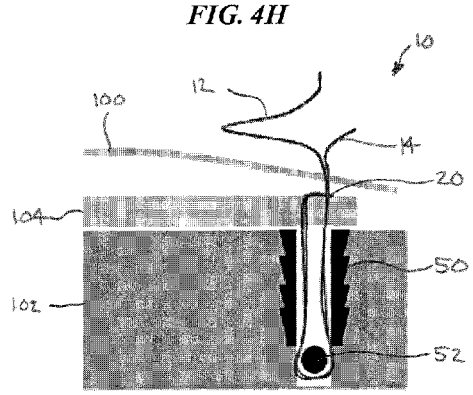
Figure 4I:
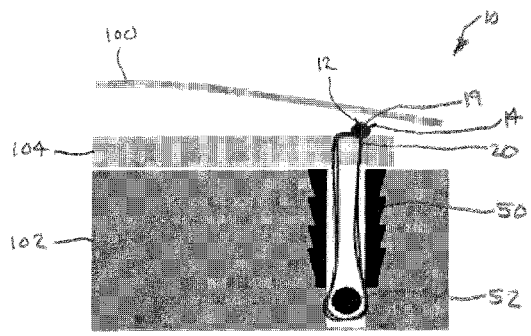

As shown in FIG. 4H, the coaxial region 30 can be disassembled such that the terminal end 14t of the second limb 14 is no longer disposed in a volume of the first limb 12. The disassembly can occur at the junction 18, for instance by untucking or pulling out the second limb 14 from the first limb 12. Alternatively, the coaxial region 30 can be removed entirely by cutting the limbs 12 and 14 at a location distal of the coaxial region 30, thereby leaving a portion of the limbs 12 and 14. In either instance, the limbs 12 and 14 can then be cinched or otherwise tied together to assist in securing a location of the collapsed snare 20, and thus the tendon 104 with respect to the bone, as illustrated in FIG. 4I. In the illustrated embodiment, a half-hitch 19 is formed by the surgeon using the first and second limbs 12, 14. A second half-hitch can be formed to lock the location of the first half-hitch 19.

Although in the illustrated embodiment the construct 10 is passed through two portions of tendon 104, alternatively the construct 10 can be passed through only one portion of tendon or tissue while the second portion of the construct 10 can be free of the tendon or tissue. Such an embodiment can be used, for example, during a labral repair. Either of the two ends 10a, 10b can be the end that is not passed through the tendon or tissue, although in some embodiments it may be useful to have the end 10a on which the snare 20 is located to not pass through tissue to minimize the possibility of unintentional collapse of the snare 20. Further, in some embodiments, rather than passing through tissue, a repair construct 10 can be coupled to tissue using other techniques, such as, for example, by wrapping the construct around the tissue.

Still further, although the method described with respect to FIGS. 4A-4I uses the suture shuttle filament 60 to locate the construct 10 in a desired location with respect to the anchor 50, in other embodiments the construct 10 can be pre-coupled to the anchor 50 that is inserted through the cannula and to the surgical location. In such embodiments, exemplary methods can begin at FIG. 4D or 4E, with the construct 10 already being coupled to the anchor 50 and the anchor 50 being fixated into bone 102 using ordinary techniques, such as by using a driver to screw or tap the anchor 50 into place.

One skilled in the art will appreciate further features and advantages of the invention based on the above-described embodiments. Accordingly, the invention is not to be limited by what has been particularly shown and described, except as indicated by the appended claims. Further, although the constructs and methods provided for herein are generally directed to surgical techniques, at least some of the constructs and methods can be used in applications outside of the surgical field. All publications and references cited herein are expressly incorporated herein by reference in their entirety.

What is claimed is:

1. A suture construct, comprising:
   a first limb having a first length;
   a second limb having a second length that is shorter than the first length;
   a coaxial region formed by a terminal end of the second limb being disposed within a volume of the first limb, the coaxial region being configured such that the terminal end of the second limb does not also pass out of the coaxial region; and
   a collapsible snare defined by the first limb and the second limb, the collapsible snare being located on one side of the coaxial region and a terminal end of the first limb being disposed on an other side of the coaxial region, the terminal end of the first limb being unconstrained,
   wherein the coaxial region is configured to be disassembled after placement of the suture construct at a surgical location so the first and second limbs can be used to secure a location of the suture construct.

2. The suture construct of claim 1, wherein the collapsible snare includes a slidable knot such that a size of an opening defined by the snare is able to be decreased by moving the slidable knot away from the coaxial region and the size of the opening is able to be increased by moving the slidable knot towards the coaxial region.

3. The suture construct of claim 1, wherein a length of the coaxial region is substantially shorter than a length of the first limb extending from the other side of the coaxial region.

4. The suture construct of claim 3, wherein the length of the coaxial region is substantially shorter than lengths of the first and second limbs on the side of the coaxial region on which the snare is located.

5. The suture construct of claim 1, further comprising a suture anchor having a filament engagement feature, a portion of the construct being slidably disposed around a portion of the filament engagement feature.

6. The suture construct of claim 5, wherein the snare extends from one side of the suture anchor and the coaxial region extends from another side of the suture anchor.

7. The suture construct of claim 5, wherein a portion of the first limb disposed on the other side of the coaxial region engages the filament engagement feature of the suture anchor such that the portion of the first limb disposed on the other side of the coaxial region extends from both sides of the suture anchor.

8. The suture construct of claim 1, wherein the first limb is cannulated at the coaxial region.

9. The suture construct of claim 1, wherein the first limb and the second limb are portions of one surgical filament.

10. The suture construct of claim 9, wherein the surgical filament comprises a braided suture.

11. A suture construct, comprising:
a first limb having a first length;
a second limb having a second length that is shorter than the first length;
a coaxial region formed by the second limb being disposed within a volume of the first limb; and
a collapsible snare defined by the first limb, the second limb, and a slidable knot such that a size of an opening defined by the snare is able to be decreased by moving the slidable knot away from the coaxial region and the size of the opening is able to be increased by moving the slidable knot towards the coaxial region, the collapsible snare being located on one side of the coaxial region and a terminal end of the first limb being disposed on an other side of the coaxial region,
wherein the collapsible snare is a first terminal end of the suture construct and the terminal end of the first limb is a second terminal end of the suture construct.

12. The suture construct of claim 11, wherein a length of the coaxial region is substantially shorter than a length of the first limb extending from the other side of the coaxial region.

13. The suture construct of claim 12, wherein the length of the coaxial region is substantially shorter than lengths of the first and second limbs on the side of the coaxial region on which the snare is located.

14. The suture construct of claim 11, further comprising a suture anchor having a filament engagement feature, a portion of the construct being slidably disposed around a portion of the filament engagement feature.

15. The suture construct of claim 11, wherein the first limb and the second limb are portions of one surgical filament.

16. A suture construct, comprising:
a first limb having a first length;
a second limb having a second length that is shorter than the first length;
a coaxial region formed by the second limb being disposed within a volume of the first limb; and
a collapsible snare that includes the first limb and the second limb and is defined by a slidable knot such that the collapsible snare extends from one side of the slidable knot and the first and second limbs extend directly out of an opposite side of the slidable knot, towards the coaxial region, the slidable knot being configured such that a size of an opening defined by the snare is able to be decreased by moving the slidable knot away from the coaxial region and the size of the opening is able to be increased by moving the slidable knot towards the coaxial region.

17. The suture construct of claim 16, wherein a length of the coaxial region is substantially shorter than a length of the first limb extending from the other side of the coaxial region.

18. The suture construct of claim 17, wherein the length of the coaxial region is substantially shorter than lengths of the first and second limbs on the side of the coaxial region on which the snare is located.

19. The suture construct of claim 16, further comprising a suture anchor having a filament engagement feature, a portion of the construct being slidably disposed around a portion of the filament engagement feature.

* * * * *